US00RE41290E

(19) United States
(12) Reissued Patent
Kimura

(10) Patent Number: US RE41,290 E
(45) Date of Reissued Patent: Apr. 27, 2010

(54) PROCESS FOR PURIFYING PHENOL-CONTAINING BISPHENOL A

(75) Inventor: Hiroaki Kimura, Kashima-gun (JP)

(73) Assignee: Mitsubishi Chemical Corporation, Tokyo (JP)

(21) Appl. No.: 11/808,251

(22) Filed: Jun. 7, 2007

Related U.S. Patent Documents

Reissue of:
(64) Patent No.: 6,951,965
Issued: Oct. 4, 2005
Appl. No.: 11/005,300
Filed: Dec. 7, 2004

U.S. Applications:
(63) Continuation of application No. PCT/JP03/09707, filed on Jul. 31, 2003.

(30) Foreign Application Priority Data

Aug. 8, 2002 (JP) ..... 2002-231473

(51) Int. Cl.
*C07C 37/68* (2006.01)

(52) U.S. Cl. ..... 568/724; 568/727; 568/728

(58) Field of Classification Search ..... 568/724, 568/727, 728

See application file for complete search history.

(56) References Cited

U.S. PATENT DOCUMENTS

| | | | |
|---|---|---|---|
| 4,942,265 | A | 7/1990 | Iimuro et al. |
| 5,324,867 | A | 6/1994 | Asaoka et al. |
| 5,874,644 | A | 2/1999 | Gammill |
| 6,307,111 | B1 | 10/2001 | Fennhoff et al. |

FOREIGN PATENT DOCUMENTS

| | | | |
|---|---|---|---|
| EP | 290179 | A1 | 12/1988 |
| JP | 05-294874 | | 11/1993 |
| JP | 6-107579 | A | 4/1994 |
| JP | 6-107579 | * | 4/1994 |
| JP | 8-325183 | A | 12/1996 |
| JP | 2000-191575 | | 7/2000 |

* cited by examiner

*Primary Examiner*—Shailendra Kumar
(74) *Attorney, Agent, or Firm*—Nixon & Vanderhye P.C.

(57) ABSTRACT

The process of the present invention comprises a first step in which crude molten bisphenol A containing phenol is supplied to a flash evaporator and separated into a gaseous phase comprising phenol and a liquid phase comprising bisphenol A and residual phenol, and a second step in which the liquid phase obtained in the first step is heated by a thin film evaporator and separated into a gaseous phase comprising phenol and a liquid phase comprising concentrated bisphenol A and residual phenol, part of the liquid phase obtained in the second step being circulated to the first step and supplied to the flash evaporator along with crude molten bisphenol A. It is possible with this process to obtain high-quality bisphenol A stably from phenol-containing bisphenol A.

9 Claims, 2 Drawing Sheets

PROCESS FOR PURIFYING PHENOL-CONTAINING BISPHENOL A

Matter enclosed in heavy brackets [ ] appears in the original patent but forms no part of this reissue specification; matter printed in italics indicates the additions made by reissue.

CROSS REFERENCE TO RELATED APPLICATION

This application is a *reissue of application Ser. No. 11/005,300, U.S. Pat. No. 6,951,965, which in turn is a* continuing application of application Ser. No. PCT/JP03/09707 filed Jul. 31, 2003 which in turn claims the priority of Japanese patent application Serial No. 2002-231473 filed Aug. 8, 2002.

TECHNICAL FIELD

The present invention relates to a process for purifying bisphenol A by removing phenol from phenol-containing bisphenol A (viz. 2,2-bis(4-hydroxyphenyl)propane).

BACKGROUND ART

Bisphenol A is an important chemical product as a base material of polycarbonate resins, epoxy resins and such, and is produced industrially on a large scale through the reaction of phenol and acetone. For isolating bisphenol A from the reaction mixture, the reaction mixture is first concentrated and then cooled to let bisphenol A crystallize as an adduct with phenol, and the adduct is subjected to a suitable solid/liquid separating means such as centrifuge to separate the crystals from the mother liquor.

This bisphenol A/phenol adduct is then melted and distilled to separate it into bisphenol A and phenol. Since bisphenol A tends to be thermally decomposed and transformed into isopropenylphenol or such when exposed to a high temperature, the distillation of the bipshenol A/phenol adduct for separation is usually carried out under reduced pressure. For instance, in Japanese Patent Application Laid-Open (KOKAI) No. 5-294874, there is described that the bisphenol A/phenol adduct is melted and supplied to a centrifugal thin film evaporator and phenol is evaporated away under reduced pressure and a pressure of not lower than 45 Torr. However, in order to remove phenol sufficiently without much raising the degree of vacuum, it needs to elevate the operating temperature, which involves the possibility of causing thermal decomposition of bisphenol A.

In Japanese Patent Application Laid-Open (KOKAI) No. 6-107579, there is described a technique in which a melt of a bisphenol A/phenol adduct is supplied to a flash evaporator and separated into a gaseous phase comprising phenol and a liquid phase where phenol is not more than 4% by weight, and this liquid phase is further supplied to a centrifugal thin film evaporator to evaporate away phenol. However, for reducing the phenol content in the liquid phase below 4% by weight by flash evaporation, it is necessary to evaporate a large amount of phenol, for which flash evaporation needs to be carried out under a high degree of vacuum or at a high temperature. However, flash evaporation under a high degree of vacuum may cause separating of bisphenol A or the bisphenol A/phenol adduct as a solid because of excessive drop of temperature. Also, when flash evaporation is carried out at a high temperature, bisphenol A may be decomposed when heated to produce isopropenylphenol or such, resulting in a deteriorated hue of obtained bisphenol A.

Japanese Patent Application Laid-Open (KOKAI) No. 63-275539 teaches that when bisphenol A is recovered from the bottom of a distillation column, part of the bottom product is circulated and fed back into the said distillation column along with the crystals or melt, or their mixture, of the said adduct, and also states that it is preferable to heat the circulating liquid by an amount of heat necessary for causing evaporation of phenol in the above operation. However, in case where the circulating liquid is heated for the purpose of evaporating a large amount of residual phenol in the flasher system, it is necessary to heat the liquid to an excess degree, so that the above proposal can not be said the best method.

As viewed above, many proposals have been made on the method of harvesting bisphenol A from phenol-containing bisphenol A by evaporating phenol, but none of them is enough satisfactory. Accordingly, the present invention is intended to provide an improved method of obtaining purified bisphenol A by evaporating phenol from phenol-containing bisphenol A.

DISCLOSURE OF INVENTION

Figure 1:
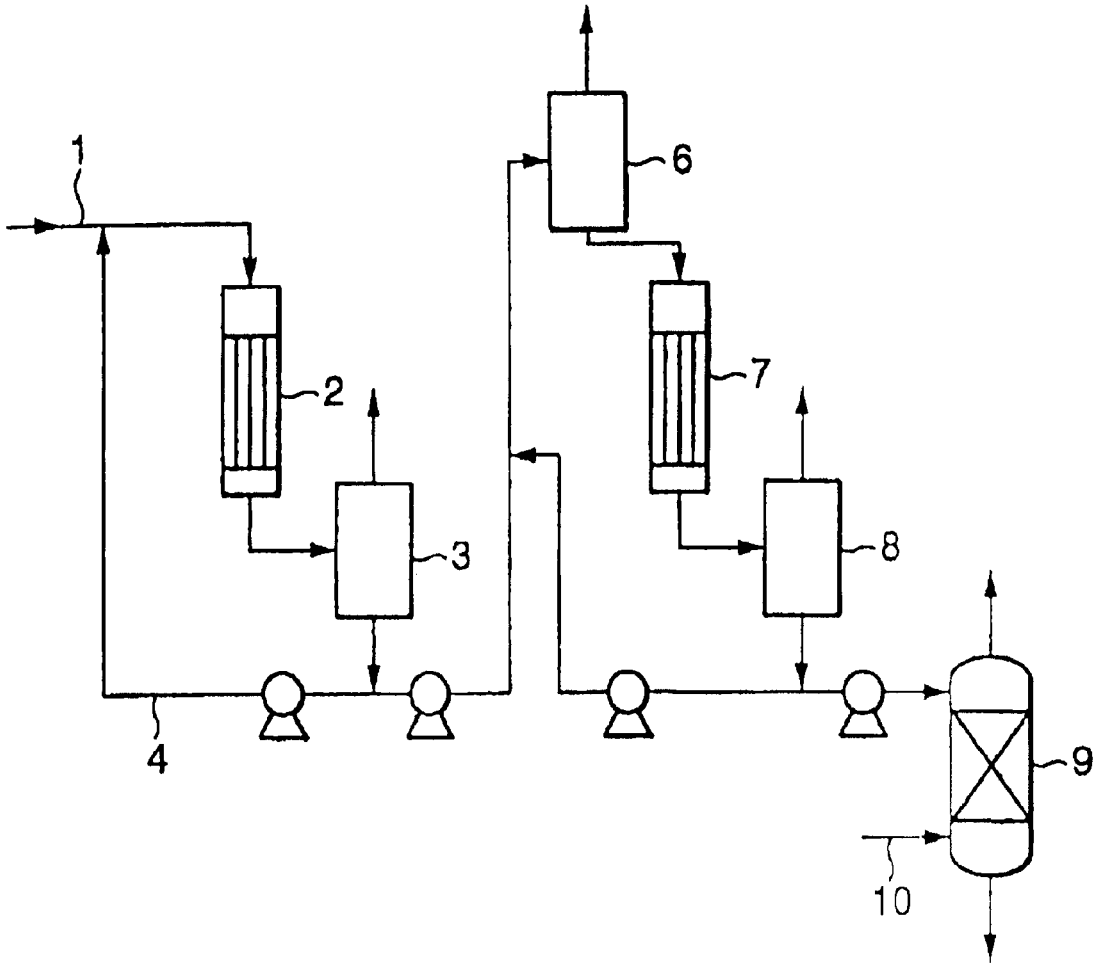
FIG. 1 is a flow sheet illustrating an embodiment of the present invention.

According to the present invention, there is provided a process for obtaining purified bisphenol A comprising a first step in which crude molten bisphenol A containing phenol is supplied to a flash evaporator and separated into a gaseous phase comprising phenol and a liquid phase comprising bisphenol A and residual phenol, and a second step in which the liquid phase obtained in the first step is heated by a thin film evaporator and separated into a gaseous phase comprising phenol and a liquid phase comprising concentrated bisphenol A and residual phenol, part of the liquid phase obtained in the second step being circulated back to the first step and fed into a flash evaporator along with the crude molten bisphenol A to effect purification of bisphenol A. It is thereby possible to harvest high-quality bisphenol A in a stabilized way from a crude melt of bisphenol A containing phenol.

The present invention will be explained in further detail below.

In the present invention, the crude molten bisphenol A containing phenol, which is to be purified, is in the first step supplied to a flash evaporator for undergoing flash evaporation to be thereby separated into a gaseous phase comprising phenol and a liquid phase comprising bisphenol A and residual (unevaporated) phenol. As the crude molten bisphenol A containing phenol, there can be used an adduct of bisphenol A with phenol (this adduct usually contains 30 to 60% by weight of phenol and other light ends), but it is preferable to use the melt from which part of phenol has already been evaporated away, as this serves for lessening the amount of phenol to be evaporated in the first step. Usually, a bisphenol A/phenol adduct from which part of phenol has been removed to concentrate bisphenol A to not less than 65% by weight, preferably not less than 70% by weight, is supplied to the first step. It is the most preferable to use an adduct in which bisphenol A has been concentrated to 73 to 77% by weight.

A thin film evaporator is preferably used for removing phenol and other light ends from a melt of bisphenol A/phenol adduct to concentrate bisphenol A. Thin film evaporators may be roughly divided into the following two types: centrifugal thin film evaporator in which a thin film of material is formed on the inner wall of the evaporating cylinder by a wiper, and natural falling-thin film evaporator in which the material is allowed to fall gravitationally along the evaporator wall surface. Both types are usable in the present invention, but the natural falling-thin film evaporator is preferred used because of structural simplicity and ease of maintenance of the apparatus. This type of evaporator is provided with a plurality of vertically arranged heating tubes and designed such that phenol and other light ends are heated and evaporated while the melt of bisphenol A/phenol adduct flows down along the wall surfaces of the heating tubes.

Intra-evaporator pressure is preferably adjusted to be *more than 60 Torr, preferably* between 60 and 400 Torr, especially between 100 and 300 Torr. The heating tubes are maintained at 160 to 220° C., preferably at 170 to 200° C. by steam heating. In order to control thermal decomposition of bisphenol A, the heating temperature is preferably set at not higher than 200° C., especially not higher than 190° C. For expediting evaporation on the other hand, the heating temperature is preferably set at not less than 170° C., especially not [les] *less* than 180° C. It is possible to let the vapor of light ends and the concentrated liquid effuse separately from each other from the thin film evaporator but preferably they are discharged as parallel flows and led into a gas/liquid separator, and after sufficient gas/liquid separation, the liquid phase is supplied to the first step. If desired, part of the liquid phase which has passed through the thin film evaporator may be mixed with the melt of the bisphenol A/phenol adduct and sent back to the thin film evaporator.

Flash evaporation in the first step is naturally conducted under a pressure lower than the operating pressure of the said thin film evaporator, usually under a pressure of not higher than 100 Torr, preferably not higher than 60 Torr, especially 10 to 60 Torr. A large amount of phenol is contained in the phenol-containing crude molten bisphenol A yielded from the thin film evaporator. Therefore, if this melt is supplied as is to the flash evaporator, temperature drops acutely with evaporation of phenol, which may cause generation of the crystals of bisphenol A in the flash evaporator. In the present invention, in order to avoid such generation of crystals of bisphenol A, the said phenol-containing crude molten bisphenol A is mixed with a concentrated solution of bisphenol A prepared in the second step to raise the concentration of bisphenol A and then supplied to the flash evaporator. This can lessen the drop of temperature in the flash evaporator. Since the melting point of bisphenol A is 156 to 157° C., the mixing rate of the concentrated solution of bisphenol A supplied from the second step in the phenol-containing crude molten bisphenol A is preferably decided so that the temperature in the evaporator will not become lower than the above-shown melting point of bisphenol A even if a desired amount of phenol has been evaporated by flash evaporation.

The liquid phase produced by flash evaporation in the first step is then heated by a thin film evaporator in the second step and separated into a gaseous phase comprising phenol and a liquid phase comprising bisphenol A and residual phenol. As the thin film evaporator, it is preferable to use a natural falling-thin film type as in the case where the light ends are evaporated from the melt of the bisphenol A/phenol adduct. The pressure in this evaporator is maintained equal to or higher than the pressure in the flash evaporator in the first step. The heating temperature is usually 170° C. to 200° C., preferably 180° C. to 190° C. It is possible to let vapor and liquid effuse separately from each other from the thin film evaporator in the second step, but preferably they are discharged out together and supplied to a gas/liquid separator to effect sufficient separation of gas and liquid. Part of the liquid phase formed by this gas/liquid separation is circulated to the first step in the same way as described above and mixed with the phenol-containing crude molten bisphenol A supplied to the first step. This liquid circulation has the effect of flash-evaporating, along with phenol, the thermal decomposition products formed by heating in the second step, in addition to its above-mentioned function to lessen the drop of temperature in flash evaporation in the first step.

The concentrated liquid of bisphenol A obtained in the second step is preferably further purified by steam stripping. Steam stripping is an operation in which the concentrated liquid of bisphenol A is supplied to a packed column from its top while steam is supplied from the bottom of the column to effect countercurrent contact between the falling liquid and the rising steam to remove phenol entrained by the steam effused from the column top. This operation is preferably conducted under the same pressure as or a lower pressure than used in the second step, usually with the column top pressure of 10 to 60 Torr. The temperature is preferably selected such that purified bisphenol A yielded from the column bottom will have a temperature of 160° C. to 220° C., preferably 170° C. to 190° C. A high temperature may induce thermal decomposition of bisphenol A. The ratio of steam to the concentrated liquid of bisphenol A supplied to the packed column is usually 2 to 8% (by weight). Steam stripping makes it possible to obtain bisphenol A with very high purity and excellent hue.

BEST MODE FOR CARRYING OUT THE INVENTION

The present invention will be explained in further detail with reference to the examples thereof.

EXAMPLE 1

A melt of an adduct of bisphenol A with phenol (56% by weight of bisphenol A, 44% by weight of phenol and 0% by weight of isopropenylphenol) was purified according to the process shown by the flow sheet of FIG. 1.

23.4 parts by weight/hr of a melt (150° C.) of a bisphenol A/phenol adduct supplied via conduit 1 and 15 parts by weight/hr of a liquid circulated from a gas/liquid separator 3 via conduit 4 were mixed and led into a natural falling-thin film evaporator 2 maintained under an internal pressure of 300 Torr. Evaporator 2 was heated with steam so that the effluent liquid would have a temperature of 180° C. The liquid and gas effusing from evaporator 2 were guided into a gas/liquid separator 3 and thereby separated into gas and liquid under 300 Torr. The concentration of bisphenol A in the effluent liquid from evaporator 2 was 73.6% by weight, and the concentration of bisphenol A in the liquid extracted from gas/liquid separator 3 was 74.5% by weight, with the concentration of isopropenylphenol being 5 ppm (by weight).

A portion (15 parts by weight/hr) of the liquid extracted from gas/liquid separator was circulated and the rest thereof was mixed with the liquid (20 parts by weight/hr) sent from a gas/liquid separator 8 and supplied to a flash evaporator 6 maintained under 15 Torr for carrying out flash evaporation. The liquid (bisphenol A concentration: 97.5% by weight, temperature: 156.7° C.) discharged from flash evaporator 6 was led as is into a natural falling-thin film evaporator 7. Evaporator 7 was heated with steam so that the effluent liquid would have a temperature of 180° C. The liquid and gas effusing from evaporator 7 were led into gas/liquid separator 8 and separated into gas and liquid. The section from flash evaporator 6 to gas/liquid separator 8 in the system was kept under the same pressure.

The concentration of bisphenol A in the liquid extracted from gas/liquid separator 8 was 98.8% by weight, with the concentration of ispropenylphenol being 6 ppm (by weight). Thus, the rise of concentration of bisphenol A of the liquid phase in evaporator 7 was 1.3% by weight. This liquid, save 20 parts by weight/hr thereof circulated, was supplied to a packed column 9. 0.5 part by weight/hr of steam was supplied to the column bottom through conduit 10 to carry out steam stripping. The phenol concentration in bisphenol A yielded from the column bottom was 10 ppm (by weight), and the hue of this product was determined to be APHA<5, indicating very high quality of the product. The results are shown in Table 1.

EXAMPLE 2

Purification of bisphenol A was conducted under the same operating conditions as in Example 1 except that the pressure of flash evaporator 6 was raised from 15 Torr to 60 Torr. The results are shown in Table 1.

EXAMPLE 3

Purification of bisphenol A was conducted under the same operating conditions as in Example 1 except that the pressure of flash evaporator was raised from 15 Torr to 60 Torr while the liquid temperature at the outlet of evaporator 7 was elevated from 180° C. to 200° C. The results are shown in Table 1.

COMPARATIVE EXAMPLE 1

Purification of bisphenol A was conducted under the same operating conditions as in Example 1 except that the pressure of flash evaporator was raised from 15 Torr to 60 Torr, that the liquid temperature at the outlet of evaporator 7 was elevated from 180° C. to 200° C., and that the circulation of part of the liquid extracted from gas/liquid separator 8 to flash evaporator 6 was suspended. The results are shown in Table 1.

COMPARATIVE EXAMPLE 2

Purification of bisphenol A was conducted under the same operating conditions as in Example 1 except that the circulation of part of the liquid extracted from gas/liquid separator 8 to flash evaporator 6 was suspended. The results are shown in Table 1. In this operation, after a while, the liquid distributor of evaporator 7 was blocked with the crystals of bisphenol A to check the flow of the liquid from flash evaporator 6 to evaporator 7. The bisphenol A concentration of the liquid at the outlet of flash evaporator 6 was 93.9% by weight and the temperature was 131.7° C.

COMPARATIVE EXAMPLE 3

Figure 2:
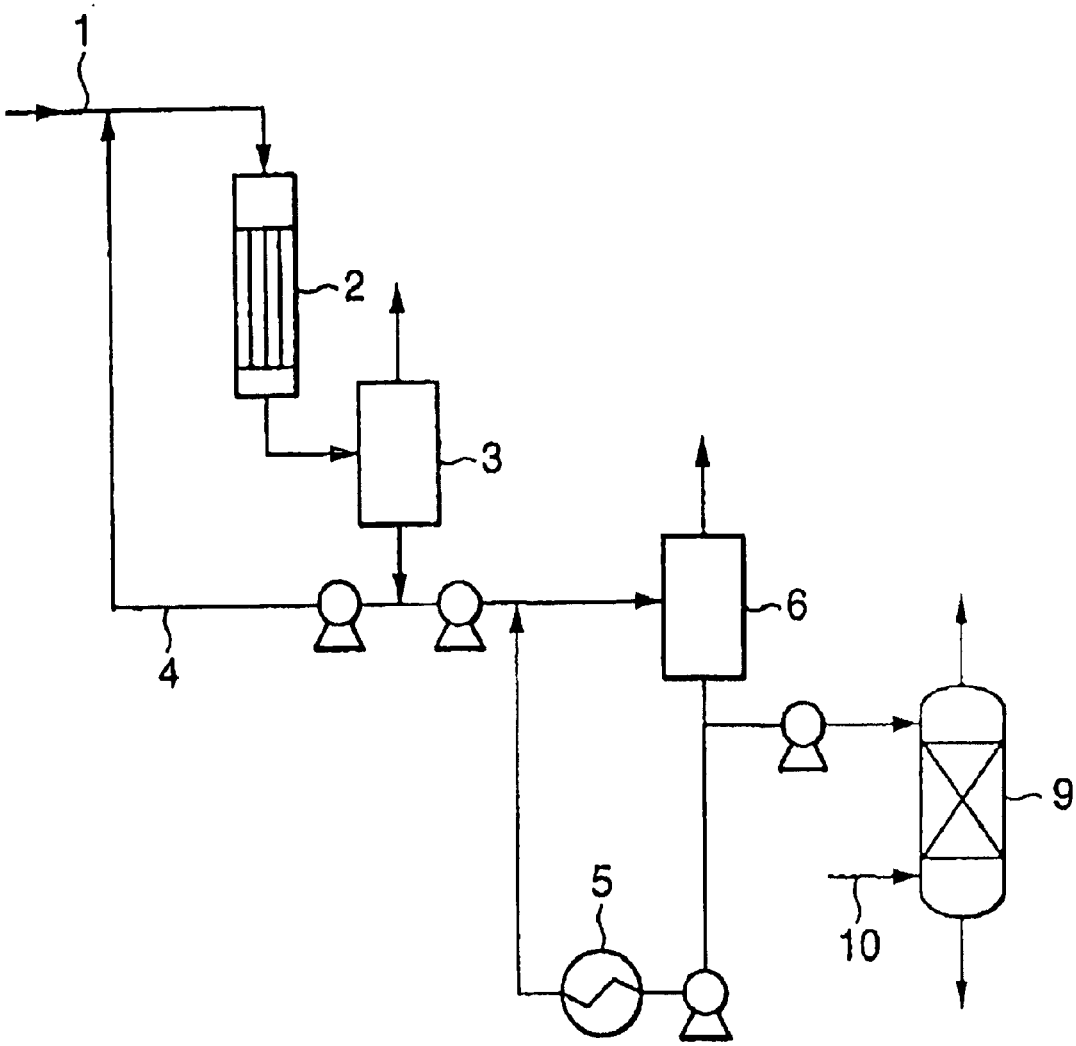
FIG. 2 is a flow sheet showing a comparative example.

A melt of a bisphenol A/phenol adduct (56% by weight of bisphenol A, 44% by weight of phenol and 0% by weight of isopropenylphenol) was purified according to the process illustrated by the flow sheet of FIG. 2.

23.4 parts by weight/hr of a melt (150° C.) of a bisphenol A/phenol adduct supplied through conduit 1 and 15 parts by weight/hr of a liquid circulated from a gas/liquid separator 3 via conduit 4 were mixed and supplied to a natural falling-thin film evaporator 2 maintained under an internal pressure of 300 Torr. Evaporator 2 was heated with steam so that the effluent liquid would have a temperature of 180° C. The liquid and gas released from evaporator 2 were led into a gas/liquid separator 3 and separated into liquid and gas under a pressure of 300 Torr. The bisphenol A concentration of the effluent liquid from evaporator 2 was 73.6% by weight and the bisphenol A concentration of the liquid extracted from gas/liquid separator 3 was 74.5% by weight, with the concentration of isopropenylphenol being 5 ppm (by weight).

The liquid extracted from gas/liquid separator 3, save 15 parts by weight/hr thereof circulated, was mixed with a liquid circulated from heater 5 at a rate of 20 parts by weight/hr and supplied to a flash evaporator 6 maintained under 60 Torr for conducting flash evaporation. Part (20 parts by weight/hr) of the effluent liquid (bisphenol A concentration: 97.5% by weight; temperature: 156.7° C.) from flash evaporator 6 was passed through heater 5 to raise the liquid temperature to 249° C. and then circulated back to gas/liquid separator 3. The rest of the liquid was supplied to a packed column 9. Steam was supplied (0.5 part by weight/hr) to the bottom of the packed column through conduit 10 to carry out steam stripping. As a result, the temperature of flash evaporator rose to 200° C., the bisphenol A concentration reached 97.2%, the IPP concentration in the liquid supplied to packed column 9 rose to 91 ppm by weight, and APHA of bisphenol A at the bottom of packed column 9 hiked to 50, verifying bad quality of the product.

TABLE 1

| | Example | | | Comp. Example | |
|---|---|---|---|---|---|
| | 1 | 2 | 3 | 1 | 2 |
| Pressure of flash evaporator (6) (Torr) | 15 | 60 | 60 | 60 | 15 |
| Liquid temperature at the outlet of thin film evaporator (7) (° C.) | 180 | 180 | 200 | 200 | 180 |
| Rate of circulation from gas/liquid separator (8) to flash evaporator (6) (parts by weight/hr) | 20 | 20 | 97.2 | 0 | 0 |
| Concentration of bisphenol A extracted from gas/liquid separator (8) (% by weight) | 98.8 | 95 | 97.2 | 97.2 | 98.8 |
| Concentration isopropenylphenol in bisphenol A extracted from gas/liquid separator (8) (% by weight) | 6 | 6 | 21 | 32 | 10 |
| Phenol concentration in bisphenol A obtained from the bottom of packed column (9) (% by weight) | 10 | 100 | 12 | 12 | 10 |
| Hue of bisphenol A obtained from the bottom of packed column (9) (APHA) | 5> | 5> | 10 | 20 | 5> |
| Operation | Stable | Stable | Stable | Stable | Blocked |

INDUSTRIAL APPLICABILITY

According to the present invention, it is possible to obtain high-quality bisphenol A stably from phenol-containing bisphenol A.

What is claimed is:

1. A process for purifying phenol-containing bisphenol A comprising a first step in which crude molten bisphenol A containing phenol is supplied to a flash evaporator and separated into a gaseous phase comprising phenol and a liquid phase comprising bisphenol A and residual phenol, [and]

a second step in which the liquid phase obtained in the first step is heated by a thin film evaporator and separated into a gaseous phase comprising phenol and a liquid phase comprising concentrated bisphenol A and residual phenol,

*wherein* part of the liquid phase obtained in the [first] *second* step being circulated to the first step and supplied to the flash evaporator along with crude molten bisphenol A, *and further comprising*

*a purification step with water vapor in which the concentrated liquid phase of bisphenol A obtained in the second step is supplied to the top of a packed column to let it flow down in the column while water vapor is blown into the column from its bottom to let it rise in the column so that phenol in the concentrated liquid phase of bisphenol A is removed entrained by water vapor.*

2. The process according to claim 1, wherein phenol-containing crude molten bisphenol A to be supplied to the flash evaporator has been passed through a light ends removing step which comprises melting an adduct of bisphenol A and phenol, and heating it by a thin film evaporator to remove the light ends including phenol.

3. The process according to claim 2, wherein removal of light ends including phenol is conducted by melting an adduct of bisphenol A and phenol, heating it by a thin film evaporator, and supplying the product to a gas/liquid separator for separating it into a gaseous phase comprising light ends including phenol and a liquid phase comprising bisphenol A and residual phenol.

4. The process according to claim 2, wherein removal of light ends including phenol is conducted [under reduced pressure and] *at* a pressure of more than 60 Torr *and not more than 400 Torr*.

5. The process according to [any one of] claim 2, wherein the thin film evaporator used in the light ends removing step is a natural falling-thin film evaporator.

6. The process according to [any one of] claim 1, wherein the thin film evaporator used in the second step is a natural falling-thin film evaporator.

7. The process according to [any one of] claim 1, wherein the first step is conducted under a pressure of not higher than 60 Torr.

8. The process according to [any one of] claim 1, wherein the separation into a gaseous phase and a liquid phase in the second step is conducted under a pressure of more than 60 Torr.

[9. The process according to any one of claim 1 further comprising a purification step with water aport in which the concentrated liquid phase of bisphenol A obtained in the second step is supplied to the top of a packed column to let it flow down in the column while water vapor is blown into the column from its bottom to let it rise in the column so that phenol in the concentrated liquid phase of bisphenol A is removed entrained by water vapor.]

10. A process for purifying phenol-containing bisphenol A comprising the steps of:

supplying a melt of an adduct of bisphenol A and phenol to a natural falling-thin film evaporator maintained under reduced pressure and a pressure of not less than 100 Torr, heating said melt to 160° C. to 220° C. to evaporate light ends including phenol to yield crude molten bisphenol A comprising bisphenol A and residual phenol, supplying said melt of adduct of bisphenol A and phenol to a flash evaporator maintained under a pressure of not more than 60 Torr to separate it into a liquid phase and a gaseous phase by flash evaporation, supplying said liquid phase to a natural falling-thin film evaporator maintained under a pressure of not more than 60 Torr, heating said liquid phase to 170° C. to 200° C. and evaporating phenol to obtain a concentrated liquid phase of bisphenol A, mixing part of said concentrated liquid phase of bisphenol A with said crude molten bisphenol A and supplying it to a flash evaporator to be subject to flash evaporation, and supplying the rest of the liquid phase to the top of a packed column to let if flow down in the column into which water vapor is being blown from the bottom so that residual phenol is entrained by water vapor and removed.

* * * * *